United States Patent [19]

McKinnie

[11] Patent Number: 5,118,890
[45] Date of Patent: Jun. 2, 1992

[54] PROCESS FOR TREATING METHYL BROMIDE MATERIALS

[75] Inventor: Bonnie G. McKinnie, Magnolia, Ark.

[73] Assignee: Ethyl Corporation, Richmond, Va.

[21] Appl. No.: 529,603

[22] Filed: May 29, 1990

[51] Int. Cl.$^5$ .............................................. C07C 17/38
[52] U.S. Cl. .................................... 570/262; 570/120
[58] Field of Search ............. 570/262, 264, 258, 102; 514/743; 424/641

[56] References Cited

U.S. PATENT DOCUMENTS 2,036,274  4/1936  Holler .................................. 570/102

FOREIGN PATENT DOCUMENTS 0026161  12/1963  Japan ................................... 556/129
0024485  11/1967  Japan ................................... 556/129
0000651   1/1970  Japan ................................... 556/129
 785289  12/1980  U.S.S.R. ............................... 570/102

OTHER PUBLICATIONS

Kirk-Othmer-*Encyclopedia of Chemical Technology*, 2nd Ed., vol. 3, pp. 766-780-(1964).
Windholz, Martha, ed. *The Merk Index*, 10th ed. p. 5908 (1983).

*Primary Examiner*—Howard T. Mars
*Assistant Examiner*—Kimberly Kestler
*Attorney, Agent, or Firm*—Edgar E. Spielman, Jr.

[57] ABSTRACT

This invention concerns the decolorizing and/or de-acidifying of methyl bromide materials by contacting same with zinc.

4 Claims, No Drawings

PROCESS FOR TREATING METHYL BROMIDE MATERIALS

BACKGROUND OF THE INVENTION

This invention relates to a process for decolorizing and/or deacidifying methyl bromide materials.

Methyl bromide, $CH_3Br$, is a colorless gas or liquid which has obtained worldwide acceptance as an agricultural fumigant. Methyl bromide is easily produced by the reaction of hydrobromic acid and methanol. The resultant methyl bromide material will generally contain a-predominant amount of methyl bromide, say 95 percent or above, and lesser amounts of water and HBr as impurities. Purification techniques are used to reduce the impurity content, however, in almost all cases, some water and HBr are unremoved. While the low levels of the remaining impurities are generally of little concern from the material's functional standpoint, they can still cause quality problems. For example, if the water and HBr containing methyl bromide material is stored in an iron or iron alloy container, it has been found that in some cases, the methyl bromide material becomes colored. The color ranges from light yellow to a dark brown. The intensity of the color appears to have some correlation with the time that the material is stored in the container.

There is resistance in the methyl bromide market to the purchase of colored material despite the fact that the colored material is still useful as a fumigant, etc. It would thus be beneficial to have a process for preventing the material from becoming colored and to have a process for decolorizing material which has become colored.

THE INVENTION

This invention relates, in one embodiment, to a process for deacidifying methyl bromide material which contains a predominant amount of methyl bromide and lesser amounts of water and HBr. The process comprises contacting the methyl bromide material with zinc metal until the desired deacidification has occurred.

In a second embodiment of this invention, there is provided a process for decolorizing a colored methyl bromide material, which process comprises contacting the colored methyl bromide material with zinc metal until the material is rendered substantially colorless.

The methyl bromide material treated by the first described embodiment can be any of such materials which are obtained by the reaction of methanol and HBr. Generally, such materials contain at least 95 weight percent methyl bromide and, as impurities, no more than about 1000 ppm water and 1000 ppm HBr. Preferred materials are those which contain no more than about 300 ppm water and no more than about 100 ppm HBr. The water and HBr impurities are present, at least in part, as a result of water being produced as a by-product and as a result of some of the HBr remaining unreacted. Also, the HBr can be present due to the hydrolysis of the methyl bromide which yields methanol and HBr. The methyl bromide material can be colorless or colored depending upon whether or not the material also contains color bodies. If color bodies are present, the process of the first embodiment will concomitantly reduce the color intensity.

The colored methyl bromide material treated by the second embodiment of this invention contains a predominant amount of methyl bromide and a coloring amount of color bodies. The identity of the color bodies is not known with certainty, but, it is believed that $FeBr_3$ may be one of such color bodies. The color body concentration in the material does not need to be substantial. The colored methyl bromide may or may not contain water and/or HBr. If it should, the treatment provided by this second embodiment will cause at least a reduction in the amount of water and HBr remaining in the treated methyl bromide material.

For both embodiments, the zinc metal is best provided in a high-surface area form as process efficiency is favored thereby. Zinc metal in the form of shot, turnings, flakes, packing, rings, galvanized tank lining, galvanized piping, etc. is suitable. Preferred is zinc metal in the form of shot.

The amount of zinc metal used is that amount which can deacidify and/or decolorize the colored methyl bromide material, as the case may be. Generally, good process efficiency can be obtained with a weight ratio of zinc metal to the methyl bromide material which is in contact with the zinc metal at any one time which is within the range for from about 0.01:1 to about 3:1. Less zinc metal can be used, however, process efficiency will suffer. More zinc metal can be used but the added cost of such use must be balanced against the advantage obtained, if any. A preferred ratio is 0.05:1 to 1.0:1.

Both embodiments of this invention can be practiced in a batch or a continuous mode. In the batch mode, a vessel of appropriate size is charged with the zinc metal and the methyl bromide material to be treated. The charging can be in any order or together. The contact time between the two is such that the so-contacted methyl bromide material, for the first embodiment, is substantially deacidified, and, for the second embodiment, is substantially decolorized. The contact time will be dependant upon the contact temperature, the presence or absence of mixing, and upon the relative amounts of zinc metal and methyl bromide material charged to the vessel. After the deacidified and/or colorless methyl bromide material has been obtained, it can be simply drained from the vessel. The drained vessel, which still holds the originally charged zinc metal, is then ready for charging with another batch of methyl bromide material. The zinc metal need not be replaced as it can be used for several treatments without substantial diminishment in its effectiveness.

In the continuous mode, the methyl bromide material can be passed through vessel containing a zinc metal bed such that the contact time between the material to be treated and the zinc metal bed is sufficient to achieve the objectives of the particular embodiment of the invention which is being practiced.

In both embodiments, the temperature and pressure during the contact period are that which provide for the methyl bromide material being in a liquid form. Generally, temperatures of from about $-20°$ C. to about $60°$ C. and pressures from about one atmosphere to about 10 atmospheres are suitable. Particularly preferred temperatures and pressures are between $0°$ C. and $35°$ C. and one atmosphere and 5 atmospheres.

In both embodiments of this invention, the treated methyl bromide material will not be as susceptible as untreated methyl bromide material to the subsequent generation of color bodies. Such a characteristic is highly beneficial to the methyl bromide material purchaser as the color quality of the product is assured irrespective of whether or not an iron or iron alloy container is used to store or package the material.

The embodiments of this invention can be particularly useful to the methyl bromide material producer who is storing the material in bulk quantities for shipment. The producer can protect against future colorization and effect decolorization, if needed, by fitting the storage tank with piping and a pump to circulate the tank contents through a canister containing a bed of zinc metal.

The iron and iron alloys which are believed to cause discoloration when in contact with methyl bromide materials containing water and HBr are exemplified by mild steel, stainless steel, iron containing nickel alloys and the like. The iron can also be provided by elemental iron.

The following examples are illustrative of the invention and are not to be taken as limiting.

EXAMPLE I

To 2.7 g of zinc shot was added 300 g of a colored MeBr material (APHA~100). After three hours the MeBr material had an APHA of ~50 and was observed to be water-white. This material was drained from the zinc.

To the remaining zinc was then added 250 g of a colored MeBr material (APHA~350). After two hours the MeBr material was observed to be water-white. This water-white material was then drained from the zinc.

Approximately 200 g of a colored MeBr material (APHA~300) was then added to the remaining zinc. The material was observed to turn water-white.

EXAMPLE II

To a 21.1328 g lump of sublimed zinc was added 300 g of a colored methyl bromide material, APHA~400. Three hours later the APHA was reduced to ~250-300. After an additional three hours the APHA was ~100-150. About sixteen hours later the material was observed to be water-white, APHA<50. After use, the zinc lump did not show a weight loss.

EXAMPLE III

In a 500 mL pressure bottle was placed 100 g of zinc lumps and 430 g of methyl bromide that contained 20 ppm of HBr, 170 ppm water, and had a color of 500 APHA. The bottle was repeatedly inverted for 10 minutes. The so-treated methyl bromide had a color of 100 APHA. After an additional 5 minutes of inverting the APHA color was below 50. Analysis of the methyl bromide 35 minutes after mixing with the zinc shows 0 ppm HBr and 165 ppm water.

What is claimed is:

1. A process for both decolorizing and deacidifying a colored methyl bromide material which contains a predominant amount of methyl bromide and less amounts of a coloring body, water and HBr, said process comprising contacting said methyl bromide material with zinc metal until deacidification has been substantially accomplished and substantially colorless methyl bromide is obtained.

2. The process of claim 1 wherein the weight ratio of said zinc metal to the colored methyl bromide material in contact with said zinc metal at any one time is within the range of from about 0.01:1 to 3:1.

3. The process of claim 1 wherein said zinc metal is in the form of shot or sublimed zinc.

4. The process of claim 1 wherein said colored methyl bromide material contains, before contacting said zinc metal, no more than about 1000 ppm water and no more than about 1000 ppm HBr.

* * * * *